(12) United States Patent
Pollock et al.

(10) Patent No.: US 7,147,662 B1
(45) Date of Patent: *Dec. 12, 2006

(54) HOOK FOR ATTACHING TO A CORPOREAL LUMEN AND METHOD OF MANUFACTURING

(75) Inventors: David T. Pollock, Burlingame, CA (US); Peter Johansson, Campbell, CA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 465 days.

This patent is subject to a terminal disclaimer.

(21) Appl. No.: 10/326,719

(22) Filed: Dec. 19, 2002

Related U.S. Application Data

(63) Continuation of application No. 09/547,822, filed on Apr. 11, 2000, now Pat. No. 6,517,573.

(51) Int. Cl.
*A61F 2/06* (2006.01)

(52) U.S. Cl. .................... 623/1.36; 623/1.15; 623/1.13

(58) Field of Classification Search ............... 606/200; 623/1.36, 1.13, 1.15
See application file for complete search history.

(56) References Cited

U.S. PATENT DOCUMENTS

| | | | |
|---|---|---|---|
| 4,739,762 A | 4/1988 | Palmaz | |
| 4,776,337 A | 10/1988 | Palmaz | |
| 5,102,417 A | 4/1992 | Palmaz | |
| 5,397,355 A * | 3/1995 | Marin et al. ................. | 623/1.2 |
| 5,423,885 A | 6/1995 | Williams | |
| 5,591,197 A | 1/1997 | Orth et al. | |
| 5,593,417 A | 1/1997 | Rhodes | |
| 5,681,346 A | 10/1997 | Orth et al. | |
| 5,733,325 A | 3/1998 | Robinson et al. | |
| 5,769,882 A | 6/1998 | Fogarty et al. | |
| 5,800,526 A | 9/1998 | Anderson et al. | |
| 5,824,036 A | 10/1998 | Lauterjung | |
| 5,824,053 A | 10/1998 | Khosravi et al. | |
| 5,824,054 A | 10/1998 | Khosravi et al. | |
| 5,836,969 A * | 11/1998 | Kim et al. ................. | 606/200 |
| 5,843,117 A | 12/1998 | Alt et al. | |
| 5,843,120 A | 12/1998 | Israel et al. | |
| 5,843,164 A * | 12/1998 | Frantzen et al. ........... | 623/1.16 |
| 5,855,802 A | 1/1999 | Acciai et al. | |
| 5,860,999 A | 1/1999 | Schnepp-Pesch et al. | |
| 5,879,381 A | 3/1999 | Moriuchi et al. | |
| 5,907,893 A | 6/1999 | Zadno-Azizi et al. | |
| 5,911,733 A | 6/1999 | Parodi | |
| 5,911,752 A | 6/1999 | Dustrude et al. | |
| 5,911,754 A | 6/1999 | Kanesaka et al. | |
| 5,913,897 A | 6/1999 | Corso, Jr. et al. | |
| 5,916,234 A | 6/1999 | Lam | |
| 5,921,995 A | 7/1999 | Kleshinski | |

(Continued)

OTHER PUBLICATIONS

U.S. Appl. No. 09/547,177 entitled: Hook for Attaching to a Corporeal Lumen and Method of Manufacturing.

*Primary Examiner*—Anhtuan T. Nguyen
*Assistant Examiner*—E Houston
(74) *Attorney, Agent, or Firm*—Fulwider Patton LLP (57) ABSTRACT

An improved hook provides for the attaching of endoluminal prosthesis within corporeal lumens. The hook is integrally formed with framing structure and is preset into an outward bend, but is resiliently flexible so as to form a substantially straight profile when compressed. The hook is capable of impinging upon the corporeal lumen and thereby securing the prosthesis. The hook may be configured for intraluminal delivery and deployment. A novel method of manufacturing said hook is also provided.

16 Claims, 6 Drawing Sheets

U.S. PATENT DOCUMENTS

| | | | |
|---|---|---|---|
| 6,231,561 B1 * | 5/2001 | Frazier et al. | 604/500 |
| 6,267,776 B1 | 7/2001 | O'Connell | |
| 6,416,530 B1 * | 7/2002 | DeVries et al. | 606/200 |
| 6,443,972 B1 * | 9/2002 | Bosma et al. | 606/200 |
| 6,517,573 B1 * | 2/2003 | Pollock et al. | 623/1.15 |
| 6,620,183 B1 * | 9/2003 | DiMatteo | 606/202 |
| 2002/0111647 A1 * | 8/2002 | Khairkhahan et al. | 606/200 |

* cited by examiner

HOOK FOR ATTACHING TO A CORPOREAL LUMEN AND METHOD OF MANUFACTURING

CROSS REFERENCES TO CO-PENDING APPLICATIONS

This application is a Continuation of application Ser. No. 09/547,822, filed Apr. 11, 2000, now U.S. Pat. No. 6,517,573.

BACKGROUND OF THE INVENTION

This invention relates to an attachment element for fixation to corporeal tissue and a method of manufacturing the same. Such an attachment element may be used to attach endoluminal prosthesis within arteries, veins and similar lumens. As such, the attachment element would be capable of intraluminal delivery.

A variety of endoluminal prosthesis currently exist which require fixation within corporeal lumens. Examples of such are grafts and stents. Grafts are artificial lumens which replace the natural lumen or reside within the natural lumen and isolate the natural tissue from blood flow.

Stents are semi-rigid tubular structures which may be used to maintain the patency of natural lumens or grafts. By providing scaffolding for the lumen, stents prevent collapse and occlusion. Stents are typically formed either by winding wire into a tubular structure or removing material from a solid tube.

Prior art grafts and stents have described the use of hooks to improve fixation of the prosthesis. These hooks were typically formed of bent wire attached to the prosthesis. The prior art also teaches integrally formed hooks on the prosthesis. These integral hooks are formed to be axially aligned with the prosthesis prior to deployment and forced outwardly upon intraluminal deployment.

What has not been taught by the prior art and was heretofore unknown is an integrally-formed, outwardly predisposed hook for attaching to a corporeal lumen. The present invention satisfies that need.

SUMMARY OF THE INVENTION

Briefly and in general terms, the present invention embodies an attachment or anchoring element (ie., protrusion, hook, barb) for fastening to corporeal tissues and a method of manufacturing the same. The attachment or anchoring element is formed as an integral portion of a metallic frame and has a preset outward bend or curve. The attachment or anchoring element is generally comprised of an elongated member and a pointed end. The pointed end is configured to impinge upon and possibly pierce corporeal tissue, plaque or other debris or disease.

In general, the present invention provides an improved attachment or anchoring element (which will be referred to herein as a hook for convenience) for fixation of endoluminal prosthesis. As such, the hook is configured for intraluminal delivery within a catheter or capsule. The hook and endoluminal prosthesis may then be delivered to a diseased or damaged portion of a corporeal lumen such as an artery or vein. Once delivered the hook may be compressed into or pierce the interior surface of the lumen. When compressed in such a fashion, the hook and prosthesis are securely fastened to the corporeal lumen.

There exists a variety of endoluminal prostheses which would benefit from the superior fixation provided by a hook which embodies the features of the present invention. Once such device, an abdominal aortic graft is used to treat abdominal aortic aneurysms. Such treatment requires the intraluminal delivery of the graft across the aneurysm. Once delivered the graft must be firmly attached to the surrounding tissue of the abdominal aorta. The present invention, in one possible embodiment, may be configured to provide secure leak-proof fixation for abdominal aortic grafts.

The hook may be formed integrally with the endoluminal prosthesis to be secured. It may also be formed separately and attached to the prosthesis by a variety of well-known means. The hook is typically formed from a metallic frame. This frame could be separate from the host prosthesis or be a portion thereof.

The hook is formed by cutting narrow incisions in the frame. These incisions define the elongated member and the pointed end. Laser-cutting is a well-known method of making such incisions. Once the hook is cut it can be bent outwardly such that the pointed end faces the direction in which the corporeal tissue will lie. This bend or curve in the hook may be permanently set by heating. Once set, the hook may be pressed back into the frame and the hook will spring back into the bent position when released due to its resilient nature.

There are a variety of configurations for the hook which are embodied in the present invention. The elongated member may have a constant cross-section throughout its length. It may also have a reducing cross-section near the pointed end. The pointed end may include one or more barbs. One configuration includes a single barb on either side of the pointed end, forming an arrowhead configuration. The pointed end may also be sharpened to further ensure fixation. Multiple hooks may be formed within a single frame. It is possible to form multiple hooks from a single set of incisions. Multiple hooks in opposing directions may provide superior fixation.

Other features and advantages of the present invention will become apparent from the following detailed description, taken in conjunction with the accompanying drawings, which illustrate, by way of example the principles of the invention.

DETAILED DESCRIPTION OF THE PREFERRED EMBODIMENTS

Figures 1, 2:
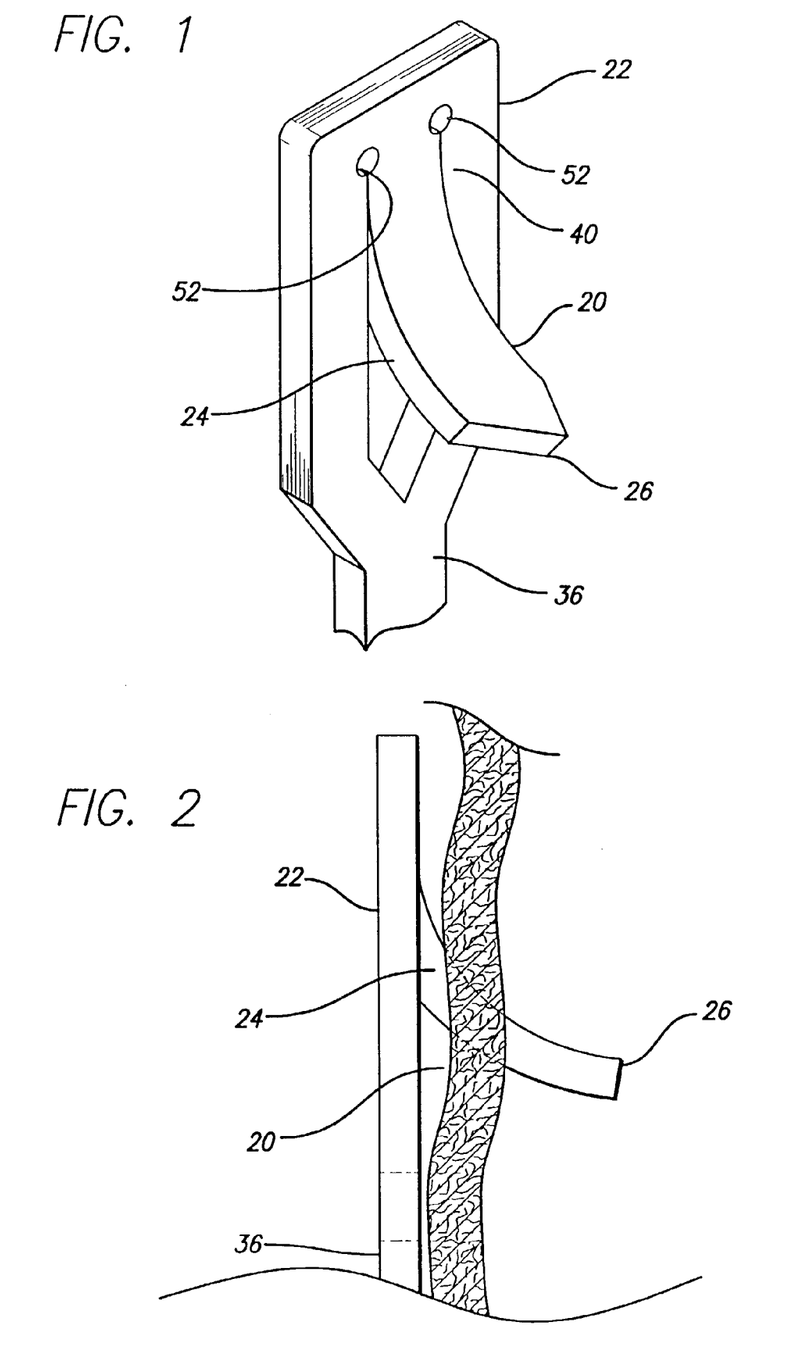
FIG. 1 is a perspective view of one embodiment of the hook and frame.
FIG. 2 is a side view of the hook and frame piercing a corporeal lumen wall.

As shown in FIGS. 1 and 2, the invention may be embodied as a hook 20 formed integrally within a frame 22. The hook 20 is comprised of an elongated member 24 and a pointed end 26. The hook 20 may be bent or curved such that the pointed end 26 extends out of the frame 22.

The hook 20 and frame 22 are configured to secure themselves to corporeal tissue. The pointed end 26 may be compressed onto corporeal tissue such that it impinges into or possibly pierces the tissue. With the curve as shown in FIG. 2, force applied downward on the frame 22 causes the hook 20 to embed into the tissue. A preferred configuration is sized to be delivered intraluminally and attach to the inside of a blood vessel. Another possibility is to configure the hook 20 and frame 22 to attach to an artificial lumen such as an endoluminal graft.

Figure 3:
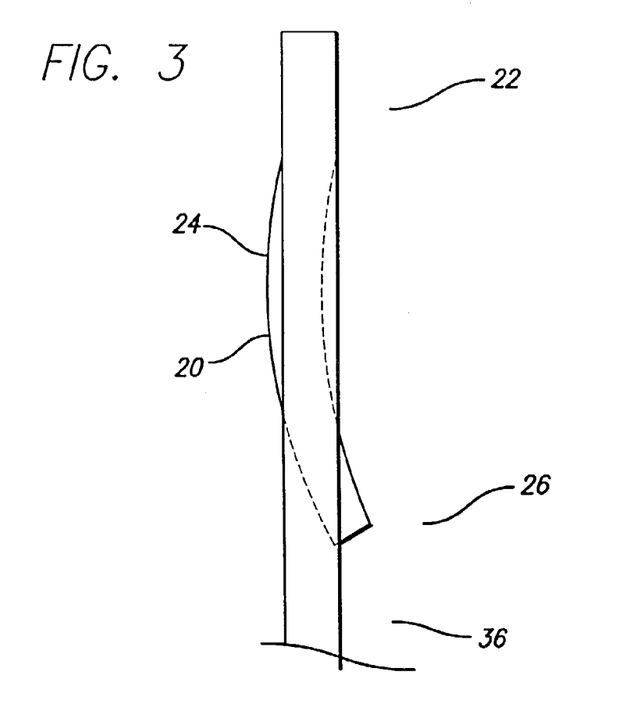
FIG. 3 is a side view of the hook and frame with the hook compressed.

In the compressed configuration, as depicted in FIG. 3, the hook 20 is preferably compressed until the hook 20 is within the bounds or circumference of the frame 22. In this manner, the combination of the hook 20 and frame 22 forms a nearly flat profile. Since the hook 20 has been deformed into a preset bend, the pointed end 26 may still extend a short distance out from the frame 22. Furthermore, due to the preset bend, the elongated member 24 may extend a short distance out of the frame 22 in the opposite direction from the pointed end 26. This compression of the hook 20 provides a very narrow cross section which facilitates loading the device into a catheter for delivery.

Figure 4:
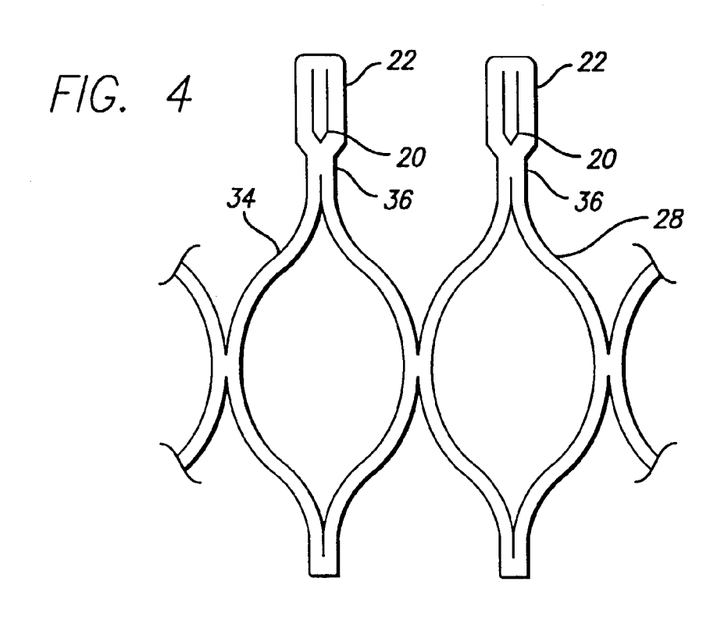
FIG. 4 is a partial front view of multiple hook and frame combinations formed integrally with a typical endoluminal prosthesis.

The hook 20 and frame 22 may be attached to or formed as part of an intraluminal endoprosthesis 28. This configuration is depicted in FIG. 4. When so attached, the function of the hook 20 and frame 22 is to secure the endoprosthesis 28 within a vascular lumen. This may be accomplished by forming or attaching the frame 22 on the endoprosthesis such that the hook 20 will embed itself into the lumen when the endoprosthesis 28 is deployed. It is to be recognized that although FIG. 4 shows hooks 20 configured at a superior end of the endoprosthesis 28, hooks 20 can also be incorporated into an inferior end of the device.

Figures 5, 6:
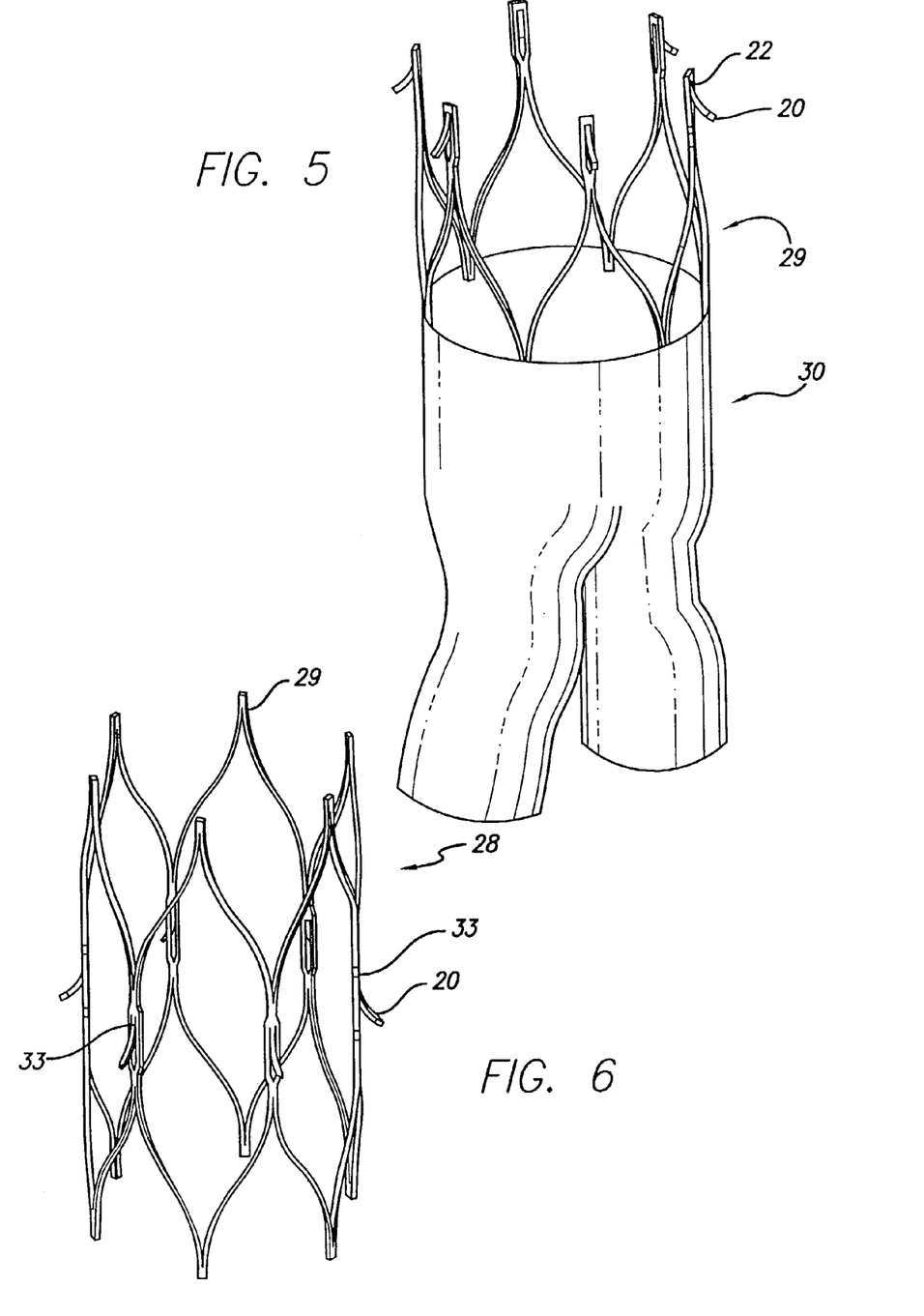
FIG. 5 is a perspective view of multiple hook and frame combinations attached to a typical endoluminal prosthesis.
FIG. 6 is a perspective view of an endoprosthesis having medial hooks.

The hook 20 and frame 22 may also form part of an attachment device 29 for a graft 30. This configuration is shown in FIG. 5. Such an arrangement may be attached to a superior end as well as inferior ends (not shown) of the graft 30. Additionally, the attachment device 29 may be affixed longitudinally separated from the graft 30 or may be attached to inside or outside surfaces thereof. The attachment device 29 expands the hook 20 into the vessel wall. The combined attachment forces of the imbedded hook 20 and the expanded attachment system 29 provide stable fixation of the endoluminal graft 30 within the vessel.

There exists a variety of devices that fit within the definitions of an intraluminal endoprosthesis 28 and a graft 30. Most of theses devices would benefit from the use of the securing devices defined herein. As shown, the same may form part of grafts which primarily replace the natural lumens or isolate them from the blood flow. Stents, which primarily ensure the patency of a lumen by resisting collapse and occlusion, can also benefit from the present invention as would implantable blood clot filters such as those often put in the vena cava.

The addition of the frame 22 and hook 20 of the present invention to existing grafts, stents and filters would provide such devices with superior fixation capability. For grafts the present invention will provide the additional benefit of leak-proof sealing of the graft to the blood vessel.

Endoluminal devices are typically collapsed for intraluminal delivery. Upon delivery to the desired location within the corporeal lumen, these devices are re-expanded. This re-expanding is accomplished in a number of ways. Balloon expansion requires the use of an angioplasty-type balloon catheter, which expands a device located about the balloon. Self-expansion uses the spring forces or super-elastic properties of the compressed device to expand outwardly once released. Shape memory metals have also been used in endoluminal devices to expand upon the addition of energy or chemicals. The expansion forces of any of these methods are sufficient to embed the appropriately placed hook 20 into a corporeal lumen. The frame 22 and hook 20 may be attached to the device such that the hook 20 is disposed radially outwardly from the device. As the device further expands radially outwardly the hook 20 is driven into the tissue of the corporeal lumen. Using several hook 20 and frame 22 combinations around the perimeter of the device ensures the most secure attachment.

Another method of securing the hook 20 allows attachment without relying upon expansion forces. The hook 20 may be impinged into the corporeal lumen by translating the hook 20 and frame 22 axially. Since the elongated member 24 is bent outward as it extends toward the pointed end 26, translating the hook 20 in the opposite direction of the elongated member's extension will force the pointed end 26 deeper into the corporeal lumen. Implanting the hook 20 and frame 22 in a position such that the axial forces of the blood flow are in this same direction will help secure the device over an extended period.

The frame 22 may be a separate device or may be a portion of the endoluminal device to which the hook 20 and frame 22 are a part. The frame 22 may be a small flat plate. Additionally since many endoluminal devices are formed from tubes, the frame 22 may be a portion thereof. that is, the frame 22 may be curved. Within the Figures, the frame 22 is depicted as a small roughly rectangular element with a connection 36 at one end. However, the frame 22 may be of any size or shape, or the frame 22 may be indistinguishable from the components of the endoluminal device from which the frame 22 is formed.

The hook 20 and frame 22 are typically formed of metal. Biocompatible stainless steel and Nitinol (Nickel Titanium Alloy), are particularly suited for this purpose. More exotic materials such as ceramics and plastics may also perform adequately.

The hook 20 may be formed in the frame 22 by first cutting incisions 40 into the frame 22. Preferably these incisions 40 are cut in such a manner as to remove the smallest amount of material from the frame 22 and hook 20, while still allowing for stress relief and freedom of movement of the hook. This preferred method leaves the hook 20 bounded on three sides by a narrow incision 40. This cutting forms the elongated member 24 and the pointed end 26. Laser cutting is a process known in the art which is preferred for making these incisions. To relieve the stresses caused by bending, additional material may be removed at the end of the incisions 40 in the form of cut-outs 52 (shown in FIG. 1).

Figure 9:
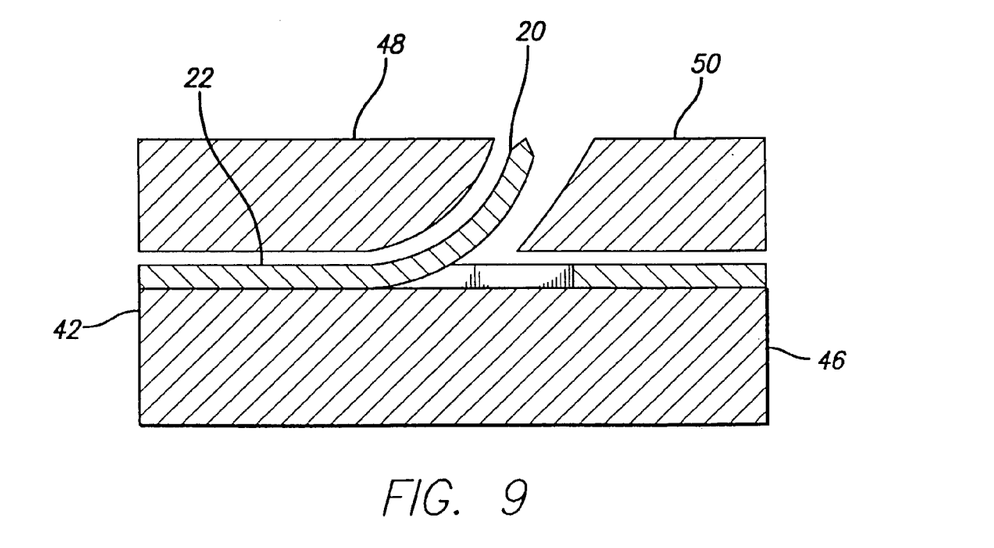
FIG. 9 is a partial cross-sectional view of a second embodiment of the mandrel assembly and a hook and frame.

With reference to FIG. 6, it is to be noted that it is also contemplated that an endoprosthesis 28 of the present invention can embody hooks 20 that are located medial the ends 29, 31 of the endoprosthesis 28. In such an arrangement, the hooks 20 can be positioned at a junction 33 between adjacent struts of adjacent cells 35 that define the endoprosthesis 28. It is to be recognized that although FIG. 9 shows a hook 20 positioned at each junction 33, for certain applications, fewer hooks 20 may be desirable.

Figure 7A:
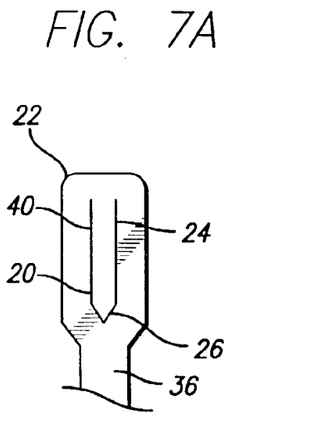
FIG. 7A is a front view of a first embodiment of the hook and frame.

Varying the configurations of the incisions 40 made in the frame 22 will provide a variety of configurations of the hook 20. As depicted in FIG. 7A the simplest configuration may be to cut parallel incisions 40 with a pointed end 26 which forms a constant cross-section elongated member 24 with a simple point.

Figure 7B:
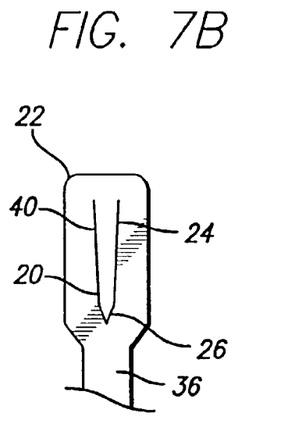
FIG. 7B is a front view of a second embodiment of the hook and frame.

Another configuration depicted in FIG. 7B has non-parallel incisions 40 which narrow towards the pointed end 26. This produces an elongated member with a cross-section which reduces toward the pointed end 26. The reduction in cross-section allows a decreasing bend radius near the pointed end 26 (See FIG. 7F). In this manner the pointed end may be pointed outwardly more towards the perpendicular which aids in impinging the corporeal tissue.

Figure 7C:
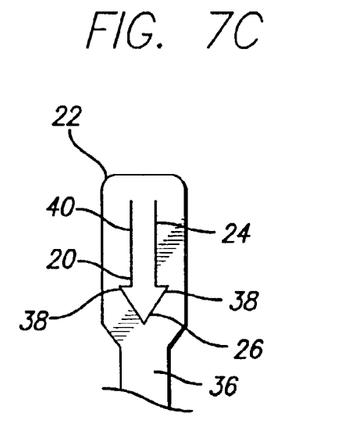
FIG. 7C is a front view of a third embodiment of the hook and frame.

Another configuration, depicted in FIG. 7C, includes barbs 38 on the pointed end 26. With two such barbs 38 the pointed end has an arrowhead configuration. These barbs 38 may help secure the hook within the corporeal lumen.

Figure 7D:
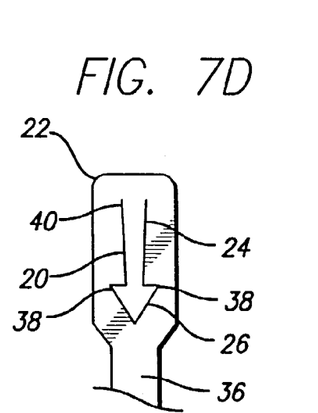
FIG. 7D is a front view of a fourth embodiment of the hook and frame.

Combining configurations, as depicted in FIG. 7D, produces a narrowing elongated member 24 with barbs 38. Such a configuration could combine the advantages of a decreasing bend radius with that of a barbed pointed end 26 (See FIG. 7F).

Figure 7E:
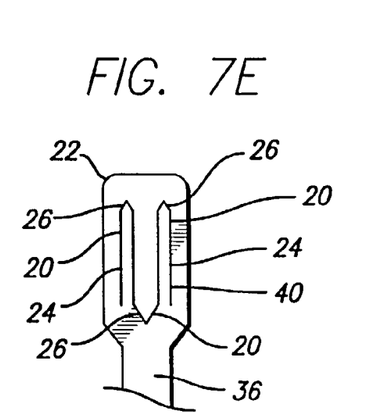
FIG. 7E is a front view of a fifth embodiment having multiple hooks on a single frame.
Figure 7F:
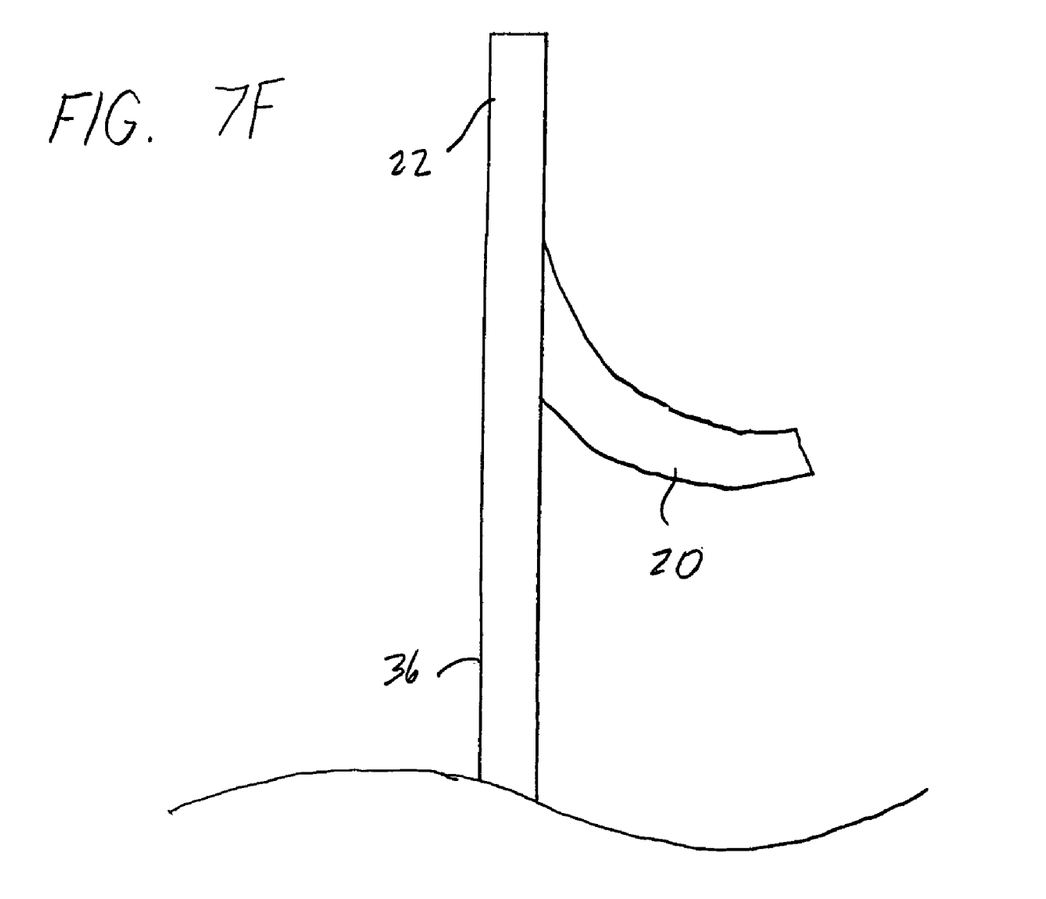
FIG. 7F is a side view of a hook having a decreasing radius of curvature.

Another configuration, depicted in FIG. 7E, creates a plurality of hooks 20 from the same incisions 40. This could form hooks 20 which project in opposing directions. Such a configuration would provide superior resistance to radial and axial loads from the corporeal lumen and blood flow.

The pointed end 26 of each of these configurations may be sharpened to improve its ability to pierce the corporeal lumen. Material may be removed from either or both the lumen-facing or frame-facing sides of the pointed end 26 to produce a sharper point.

The preferred method of manufacturing the hook 20 and frame 22 includes cutting the hook 20 out of the frame 22 using narrow incisions 40. Several methods of making such incisions 40 in metal are well known. Possible examples are laser cutter, photo-etching and chemical etching.

Once the hook 20 is cut into the frame 22, it may be bent away from the frame 22. This may be accomplished manually by using tweezers to force the pointed end 26 of the hook 20 away from the frame 22. If the hook 20 and frame 22 are formed as part of an endoluminal device, the device may be mounted on a mandel 42 with pins 44 or similar means to force the pointed end 25 of the hook 20 away from the frame 22.

Figure 8:
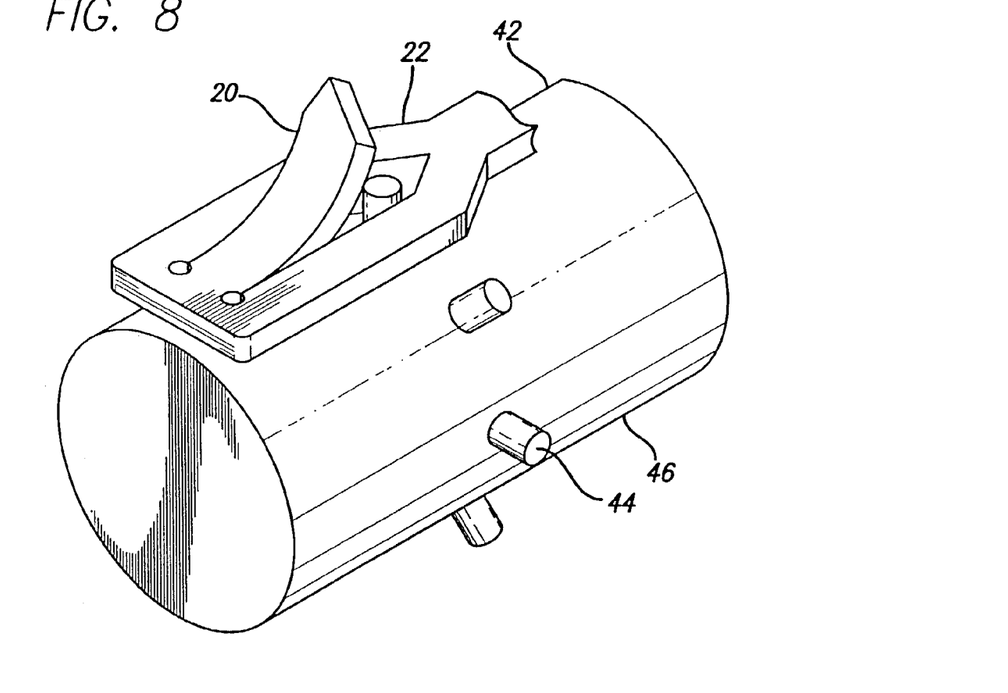
FIG. 8 is a perspective view of a first embodiment of a mandrel assembly for bending the hook.

As depicted in FIG. 8, the mandrel 42 is preferably configured as a cylindrical shaft with pins 44 appropriately spaced about the circumference of the shaft. A frame 22 may be pressed against the shaft 46 such that a pin 44 forces the hook 20 outwardly. This configuration can be maintained while the hook 20 is heat sent to be permanently predisposed with an outward curve. Another preferred configuration for the mandrel, as depicted in FIG. 9, includes a cylindrical shaft 46, a convex outer ring 48 and a concave outer ring 50. A curved gap between the outer rings forces the hook 20 into a predetermined bend. This configuration of shaft and rings may be clamped together for heat setting.

After bending, the hook 20 may be permanently-deformed into the curved configuration by heat setting the material. For a Nitinol hook 20 and frame 22 combination heating at 550° C. for ten minutes is sufficient. A ceramic or plastic hook 20 and frame 22 combination might be formed in a bent configuration.

With a permanently deformed hook 20, the hook 20 may still be compressed into alignment with the frame 22 without losing the preset curve. Thus, the hook 20 may be compressed into the frame for intraluminal low-profile delivery, and then deployed in the curved configuration by releasing. This is a significant advantage in producing a fixation device small enough to be delivered intraluminally.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A mechanism for securing an endoprosthesis within a corporeal lumen, the mechanism comprising:
    a frame element with incisions formed therein, the frame element having a substantially tubular shape and lacking concentrically overlapping structure;
    the incisions forming an elongated member having a pointed end, the elongated member being bounded by the frame element; and
    the elongated member bent away from said frame element wherein the elongate member has a permanent curve.

2. The mechanism of claim 1, wherein the elongated member has parallel straight sides defining a constant width.

3. The mechanism of claim 1, wherein the elongated member has non-parallel straight sides defining a narrowing width towards the pointed end.

4. The mechanism of claim 1, wherein the elongated member is resilient so as to be compressed into a position within the circumference of the frame element when constrained and to extend outside the circumference of the frame element when unconstrained.

5. The mechanism of claim 1, wherein the elongated member has a permanent constant radius curve.

6. The mechanism of claim 1, wherein the elongated member has a permanent curve of decreasing radius.

7. The mechanism of claim 1, wherein the pointed end includes at least one barb.

8. The mechanism of claim 1, wherein the pointed end is sharpened.

9. The mechanism of claim 1, wherein the mechanism is integrally formed into an endoluminal prosthesis.

10. A connector for fastening a device to corporeal tissues, said connector comprising:
    a substantially tubular body lacking concentrically overlapping structure;
    a hook having two sides and a point and being bounded by the tubular body;
    said sides and said point defined by narrow slits in the connector; and
    said hook having a permanent bend that forms a permanent curve.

11. The connector of claim 10, wherein the sides of the hook are parallel and straight and define a constant width.

12. The connector of claim 10, wherein the sides of the hook are non-parallel and straight and define a narrowing width towards the point.

13. The connector of claim 10, wherein the hook forms a permanent constant radius curve.

14. The connector of claim 10, wherein the hook forms a permanent curve of decreasing radius.

15. The connector of claim 10, wherein the point is formed in an arrowhead configuration.

16. An endoluminal prosthesis, comprising:
a substantially tubular frame element, the frame element lacking concentrically overlapping structure; and
at least one protrusion cut out of said frame element having a resiliently flexible bend formed therein, wherein the at least one protrusion has a permanent curve the at least one protrusion being bounded by the frame element and the at least one protrusion having a pointed end.

* * * * *